US00PP30788P2

(12) United States Plant Patent
Ranney

(10) Patent No.: US PP30,788 P2
(45) Date of Patent: Aug. 13, 2019

(54) TRIPLOID INTERSPECIFIC HYBRID FLOWERING PEAR TREE NAMED 'NCPX2'

(50) Latin Name: ***Pyrus* x *triploida***
Varietal Denomination: NCPX2

(71) Applicant: North Carolina State University, Raleigh, NC (US)

(72) Inventor: Thomas G. Ranney, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 15/932,716

(22) Filed: Apr. 11, 2018

(51) Int. Cl.
*A01H 5/00* (2018.01)
*A01H 6/74* (2018.01)

(52) U.S. Cl.
USPC ..... Plt./177

(58) Field of Classification Search
USPC ..... Plt./177
See application file for complete search history.

(56) References Cited

PUBLICATIONS

J Frank Schmidt & Song Co., Reference Guide, (p. 58; "Chastity Pear™") Jan. 2018, 2 pages.
Phillips, Whitney D. et al. "Fertility and Reproductive Pathways of Triploid Flowering Pears (Pyrus sp.)", HortScience, 51(8) 968-971 (2016).

*Primary Examiner* — Susan McCormick Ewoldt
(74) *Attorney, Agent, or Firm* — Myers Bigel, P.A.

(57) ABSTRACT

'NCPX2' is a new triploid, interspecific hybrid flowering pear with a broadly pyramidal habit, white flowers, multi-coloured fall foliage, resistance to fire blight, and significantly reduced fertility.

3 Drawing Sheets

Latin name of the genus and species: The Latin name of the novel plant variety disclosed herein is *Pyrus* x *triploida*.

Variety denomination: The inventive triploid, interspecific hybrid of *Pyrus calleryana* (tetraploid) x *Pyrus* 'Silver Ball' (diploid hybrid) disclosed herein has been given the varietal denomination 'NCPX2'.

BACKGROUND OF THE INVENTION

The present invention comprises a new and distinct hybrid flowering pear cultivar hereinafter referred to by the cultivar name 'NCPX2'. This new flowering pear was developed through a breeding program in Mills River, N.C. 'NCPX2' was selected from an $F_1$ population of seedlings grown from a controlled cross of an induced tetraploid *Pyrus calleryana* (H2002-031-010) (female parent; unpatented) x *Pyrus* 'Silver Ball' (diploid hybrid) (male parent; unpatented). The first asexual propagation of 'NCPX2' was carried out in August 2010 by budding in Mills River, N.C. and has been asexually reproduced repeatedly by budding over a 5-year period. 'NCPX2' propagates readily from budding using chip budding in mid-summer. 'NCPX2' has been found to retain its distinctive characteristics through successive asexual propagations.

SUMMARY OF THE INVENTION

The following are the unique and distinguishing characteristics of this new cultivar when grown under standard horticultural practices in Mills River, N.C.

1. Triploid selection with greatly reduced fertility.
2. An upright, pyramidal form with white flowers.
3. Resistance to fire blight.
4. Showy fall foliage color.

BRIEF DESCRIPTION OF THE PHOTOGRAPHS

This new flowering pear is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new pear.

DETAILED BOTANICAL DESCRIPTION

Figure 1:
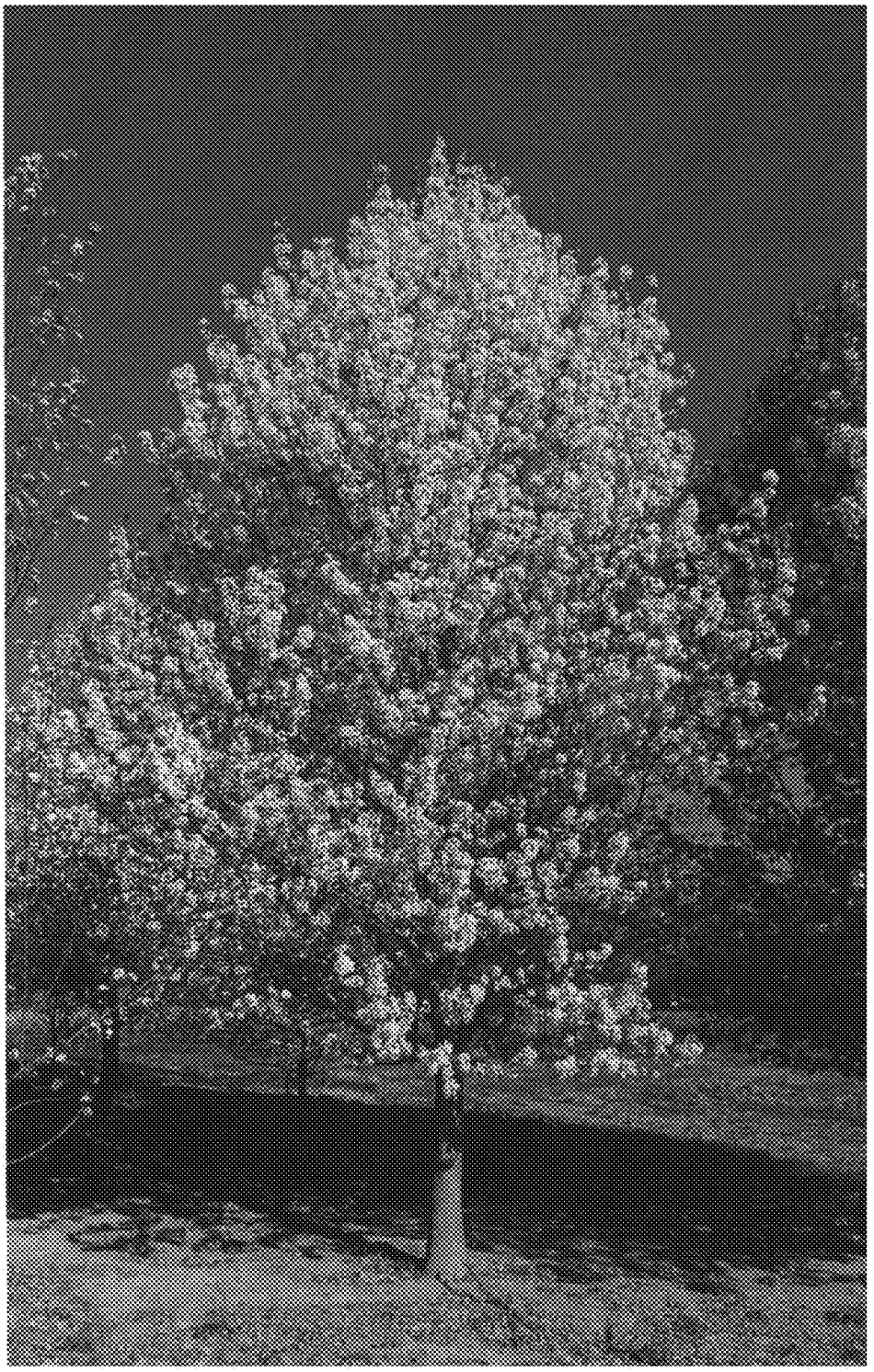
FIG. 1 is a photograph demonstrating the upright pyramidal form of an eight year old tree of 'NCPX2'.
Figure 2:
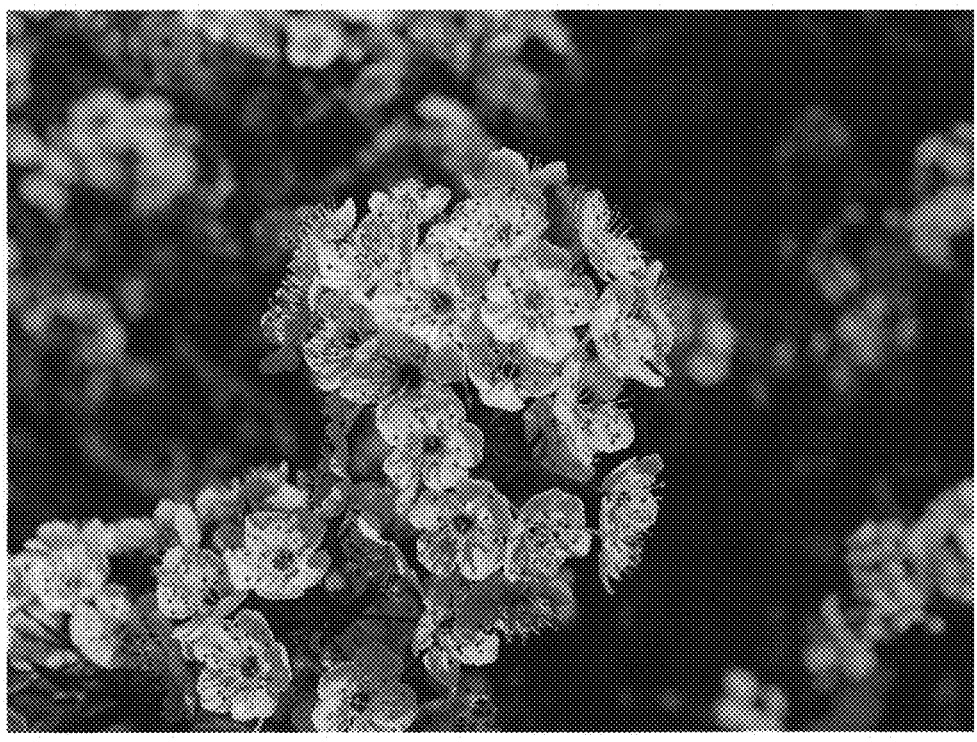
FIG. 2 is a photograph showing the white flowers from an eight year old tree of 'NCPX2'.
Figure 3:
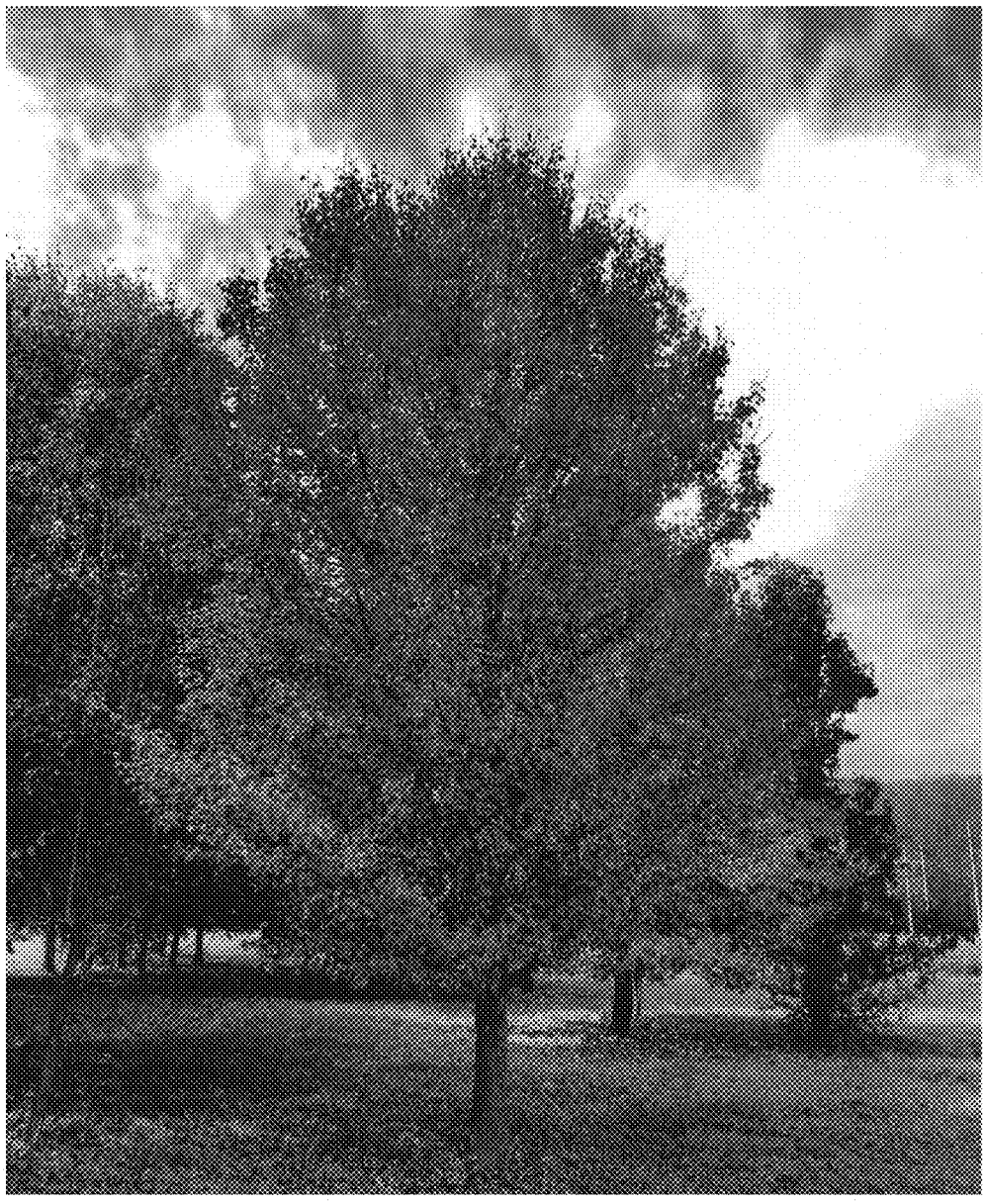
FIG. 3 is a photograph showing fall foliage colors of a nine year old tree of 'NCPX2'.

The following is a detailed description of the botanical characteristics of the new and distinct variety of interspecific hybrid flowering pear known by the denomination 'NCPX2'. The detailed description was taken on the original nine-year-old tree growing in Mills River, N.C. All colors cited herein refer to The Royal Horticultural Society Colour Chart (The Royal Horticultural Society (R.H.S.), London, 2015, 6th Edition). Where specific dimensions, sizes, colors, and other characteristics are given, it is to be understood that such characteristics are approximations or averages set forth as accurately as practicable.

TECHNICAL DESCRIPTION OF THE VARIETY

Classification:

*Botanical name.*—*Pyrus* x *triploida* 'NCPX2'.

*Common name.*—Triploid hybrid flowering pear.

Parentage: $F_1$ hybrid of *Pyrus calleryana* H2002-031-010 (tetraploid) x *Pyrus* 'Silver Ball' (diploid interspecific hybrid of uncertain parentage, possibly *P. fauriei* x *P. betulaefolia*).

Plant description:

*Growth habit*.—Upright pyramidal. Height: 8 m after 9 years. Width: 6 m after 9 years.

*Shoots and stems*.—Branching habit: Upright spreading. Lateral branch length: 3 to 6 m. Diameter: 3 to 9 cm. Internode length: 2 to 5 cm. Color: Brown (N200B). Trunk texture: Smooth to rough. Trunk color: Brown (N200C to N200D).

*Mature leaves*.—Type: Simple. Persistence: Deciduous. Arrangement: Alternate. Shape: Ovate. Apex: Acuminate. Base: Rounded. Venation: Pinnate. Margin: Serrulate. Texture: Glabrous both upper and lower.

*Emerging leaves*.—Color: Upper surface: Yellow-Green (146A). Lower surface: Yellow-Green (146B).

*Mature leaves during growing season*.—Color: Upper: Green (137A). Lower: Yellow-Green (146B). Length of lamina: Avg. 6.1 cm (range 5.5 to 7.0 cm). Width: Avg. 4.6 cm (range 3.5 to 5.0 cm). Petiole: Length: Avg. 3.0 cm (range 2.5 to 4.0 cm). Width: 0.1 cm. Color: Yellow-Green (146D).

*Mature leaves, fall color*.—Variable. Including Brilliant Orange Yellow (21B), Vivid Red (46C), and Deep Red (53A).

*Inflorescence*.—Bud length: 0.5-0.6 cm. Bud diameter: 0.8-1.0 cm. Bud shape: Ovate. Bud color: Green-White (157C) with Red-Purple (63C) on tip.

*Individual flowers*.—Diameter: 1.5-2.0 cm. Depth: 0.6-0.8 cm. Stamen: Number: 19-22. Anther color: Red-Purple (63A). Filament color: Green-White (157D). Pistil: Number: 2. Stigma: Shape: Rounded. Color: Greyed-Green (193A). Style: Length: 0.5-0.6 cm. Color: Yellow-Green (144D). Ovary color: Green (138A). Petals: Arrangement: Star. Number: 5 petals. Shape: Elliptic. Margin: Entire. Tip: Obtuse. Length (at anthesis): 0.8-1.0 cm. Width (at anthesis): 0.7-0.9 cm. Color when opening: Green-White (157D). Color fully opened: White (NN155C).

*Fruit*.—Pome: 4 locules. Size: 0.5-1.0 in. diameter. Shape: Round to ovoid. Color: Gray orange to gray brown (including 177B, N199B, N199D). Lenticels: Many small, circular on surface. Calyx: Mostly deciduous. Length: 0.1-0.11 in. Diameter: 0.08-0.1 in. Pedicel: Length: 0.55-1 in. Diameter: 0.03-0.05 in. Color: Green (132B).

Disease and insect resistance: No significant disease or insect pests have been observed. 'NCPX2' was found to have a high level of resistance to fire blight (see data below).

Cold hardiness: At least USDA zone 5b; testing has not been completed in colder zones.

Nomenclature: To help clarify the nomenclature of *Pyrus* spp. hybrids, nothospecies *Pyrus* x *triploida* Ranney is proposed for the hybrid species name in accordance with Article H.3-5 (McNeill et al., 2012). The new hybrid species is described as follows: Nothospecies *Pyrus* x *triploida* Ranney, a triploid, interspecific hybrid between *Pyrus calleryana* Decne. and another *Pyrus* L. species or hybrid. Primary diagnostic characteristics are a 2C holoploid relative genome size of approximately 1.88±0.12 (Standard Error) pg reflecting an intermediate triploid between tetraploid 2.63±0.06 (SE) pg and diploid 1.25±0.05 (SE) pg parents (Following methods of Phillips et al., 2016).

Typification: *Pyrus* x *triploida* Ranney, nothosp. nov.

Type: United States, N.C., Mills River, 2C relative genome size of 1.93 pg, 8 m tall, 6 m wide, upright pyramidal form, NCSU H2008-049-145, 11 Nov. 2017, Ranney MCIL 2017-001 (holotype: NCSC, here designated; isotype NA).

MOPHOLOGICAL COMPARISONS WITH OTHER TAXA

A comparison of morphological characteristics between 'NCPX2' and other commercial flowering pear cultivars is presented in Table 1.

TABLE 1

Morphological comparison of 'NCPX2' with other commercial flowering pear cultivars

| | Cultivars | | | | |
|---|---|---|---|---|---|
| Trait | *Pyrus calleryana* 'Cleveland Select' (unpatented) | *Pyrus pyrifolia* 'Ohara Beni' (unpatented) | *Pyrus* 'NCPX1' (U.S. Plant Pat. No. 26,539) | *Pyrus* 'NCPX2' | *Pyrus* 'Silver Ball' (unpatented) |
| Tree growth Habit | Upright pyramidal | Upright columner. | Very narrow fastigate | Upright pyramidal | Compact, round, dwarf |
| Tree Height (after 8 years) | 8 m | 8 m | 8 m | 8 m | 4 m |
| Tree Width (after 8 years) | 6 m | 5 m | 2m | 6 m | 4 m |
| Flower bud color | White (N155A) | Red purple (53C to 63A) | Red purple (53C to 63A) | Green-white (157C) with Red-Purple (63C) on tip. | Green-White (157B) |
| Flower petal color when opening | White (N155A) | White (N155A) with some pink blush (63A, 58C, and 65A) | White (N155A) with some pink blush (63A, 58C, and 65A) | Green-White (157D) | Green white (157D) |
| Flower petal color when fully opened | White (N155A), | White (N155A), | White/ pink (155B) | White (NN155C) | White (N155) |
| Flower diameter | 1.0 to 2.0 cm | 2.5 to 3.3 cm | 3.1 to 3.6 cm | 1.5-2.0 cm | 1.0 to 2.5 cm |

FIRE BLIGHT RESISTANCE

Disease resistance to fire blight was evaluated following the procedures of Bell et al, (2004). Briefly, a virulent strain of *Erwinia amylovora* (E2002a) was prepared from 24 hour old cultures grown on nutrient agar. Three actively growing shoots were inoculated in May 2012 by bisecting the youngest leaves with a pair of scissors that had been dipped into the inoculum prior to each cut. The disease lesion length and total length of the current season's growth of the inoculated shoot were measured 40 days following inoculation. The severity of infection was expressed as the length of the fire blight lesion as a percentage of overall shoot length. 'NCPX2' was found to have a high level of resistance to fire blight with a mean lesion length of 0.8% following controlled inoculations (Table 2). No signs or symptoms of fire blight have been observed on 'NCPX2' as the result of natural infection over the last 8 years.

TABLE 2

Comparison of tire blight resistance among 'NCPX2' and other commercial flowering pear Cultivars.

| Cultivar | Disease severity - 2012 (% lesion length) Range | Mean. |
|---|---|---|
| 'Ohara Beni' | 100-100 | 100 |
| 'Cleveland Select' | 0-20 | 6.6 |
| 'NCPX1' | 0-0 | 0.0 |
| 'NCPX2' | 0-3 | 0.8 |

REPRODUCTIVE CHARACTERISTICS

Female fertility of selected triploid pears, including 'NCPX2' (H2008-049-145) was evaluated and published by Phillips et al. (2016) with a summary presented in Table 3. Female fertility was characterized by evaluating fruit set, seeds per fruit, seed germination, seedlings per flower, and percent relative fertility [(seedlings per flower for triploid/seedlings per flower for diploid control)×100], outdoors with favorable cross pollination conditions. Flow cytometry was used to determine relative genome sizes and ploidy levels. Relative fertility of 'NCPX2' was 0.86% of the most fertile diploid control, a reduction of 99.14%. Furthermore, the limited seedlings that did germinate from triploids maternal parents, including 'NCPX2', were determined to be primarily abnormal aneuploids with non-standard chromosome numbers.

TABLE 3

Ploidy, relative 2C genome size, and fertility characteristics for 'NCPX2' and selected diploids as published by Phillips et al. (2016).

| Selection | Ploidy (X) | Relative genome size (pg) | Fruit set (%) | Seeds/fruit | Germination (%) | Seedlings/flower | Relative fertility[Z] (%) |
|---|---|---|---|---|---|---|---|
| 'NCPX2' (H2008-049-145) | 3 | 1.93 ± 0.01 | 3.46 ± 0.07 | 2.05 ± 3.48 | 5.22 ± 0.11 | 0.01 ± 0.01 | 0.86 |

TABLE 3-continued

Ploidy, relative 2C genome size, and fertility characteristics for 'NCPX2' and selected diploids as published by Phillips et al. (2016).

| Selection | Ploidy (X) | Relative genome size (pg) | Fruit set (%) | Seeds/fruit | Germination (%) | Seedlings/flower | Relative fertility[Z] (%) |
|---|---|---|---|---|---|---|---|
| Diploid 1 | 2 | 1.26 ± 0.02 | 9.80 ± 0.07 | 3.89 ± 2.93 | 38.61 ± 0.11 | 0.13 ± 0.08 | 16.73 |
| Diploid 2 | 2 | 1.22 ± 0.01 | 11.06 ± 0.11 | 3.24 ± 0.51 | 25.45 ± 0.49 | 0.13 ± 0.35 | 16.3 |
| Diploid 3 | 2 | 1.23 ± 0.01 | 46.76 ± 0.22 | 3.16 ± 0.72 | 52.83 ± 0.15 | 0.80 ± 0.62 | 100.00 |

[Z]Calculated as (seedlings/flower)/(0.80), where 0.80 is the number of seedlings per flower of the most fertile diploid control, 'NCPX2' is distinguished from other flowering pear cultivars by its unique combination of traits including a triploid cytotype with a 2C genome size of approximately 1.93 pg, an upright pyramidal form, white flower petals, high resistance to fire blight, and low female fertility.

CITATIONS

Bell, A. C., T. G. Ranney, and T. A. Eaker. 2004. Resistance to fire blight among flowering pears and quince. *HortScience* 40(2):413-415.

McNeill, J., F. R. Barrie, W. R. Buck, V. Demoulin, W. Greuter, D. L. Hawksworth, P. S. Herendeen, S. Knapp, K. Marhold, J. Prado, W. F. Rrud'homme Van Reine, G. F. Smith, J. H. Wiersema, and N. J. Turland. 2012. International code of botanical nomenclature for algae, fungi, and plants (Melbourne Code). Költz Sci. Books, Oberreifenberg, Germany.

Phillips, W. D., T. G. Ranney, D. H. Touchell, and T. A. Eaker. 2016. Fertility and reproductive pathways of triploid flowering pears (*Pyrus* sp.). *HortScience* 51(8):968-971.

What is claimed is:

1. A new and distinct triploid, interspecific hybrid flowering pear tree named 'NCPX2' as illustrated and described herein.

* * * * *